United States Patent [19]

Sigwalt et al.

[11] 4,181,684
[45] Jan. 1, 1980

[54] DIPHENYL COMPOUNDS THAT ARE INTERMEDIATES IN PREPARATION OF POLYMERIZATION INITIATORS

[75] Inventors: Pierre Sigwalt, Saint Michel sur Orge; Patrick Guyot, Paris; Michel Fontanille, Montmorency; Jean-Pierre Vairon, Paris, all of France

[73] Assignee: Societe Chimique des Charbonnages—CdF CHIMIE, Paris, France

[21] Appl. No.: 822,195

[22] Filed: Aug. 5, 1977

Related U.S. Application Data

[62] Division of Ser. No. 693,730, Jun. 7, 1976, Pat. No. 4,067,917.

[30] Foreign Application Priority Data

Jun. 6, 1975 [FR] France .................. 75 17716

[51] Int. Cl.² ........................... C07C 15/14
[52] U.S. Cl. ................... 585/25; 526/173; 585/320; 585/469
[58] Field of Search .................. 260/668 C, 668 R

[56] References Cited

U.S. PATENT DOCUMENTS

| | | | |
|---|---|---|---|
| 2,614,130 | 10/1952 | Pines et al. | 260/668 C |
| 2,957,036 | 10/1960 | Markus | 260/668 C |
| 3,441,625 | 4/1969 | Bargeron et al. | 260/668 C |
| 4,035,431 | 7/1977 | Charbonneau | 260/668 C |

OTHER PUBLICATIONS

Chem. Ab. 74: 111743s, 1971.
Chem. Ab. 79: 146153e, 1973.
Chem. Ab. 84: 4563t, 1976.

*Primary Examiner*—Veronica O'Keefe
*Attorney, Agent, or Firm*—Finnegan, Henderson, Farabow & Garrett

[57] ABSTRACT

Organo-lithium compounds of the formula:

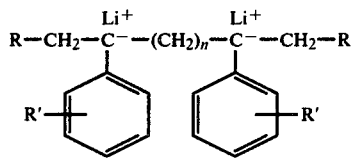

wherein R is an alkyl group of up to 5 carbon atoms, R' is either hydrogen or an alkyl group of up to 5 carbon atoms and n is an integer from 2 to 10. These bifunctional organo-lithium compounds are prepared without the use of any polar or complexing agent and are useful as polymerization initiators for the production of block copolymers.

3 Claims, No Drawings

DIPHENYL COMPOUNDS THAT ARE INTERMEDIATES IN PREPARATION OF POLYMERIZATION INITIATORS

This is a continuation, division of application Ser. No. 693,730, filed June 7, 1976 U.S. Pat. No. 4,067,917.

The present invention relates to novel organo-lithium compounds. More particularly, the present invention relates to new, bifunctional organo-lithium compounds, to a process for their preparation and to their use as polymerization initators in the formation of three component-block copolymers.

To form three block copolymers such as ABA where B is a diene and A is an anionically polymerizabale monomer, it is generally recognized in the art that these copolymers can be prepared by two different processes. In one process consisting essentially of three steps, successive additions of first monomer A, then diene B, and finally, monomer A are made to a reaction mixture. In another process the block copolymer is prepared by an essentially two-step process in which a block copolymer of AB is first formed with B being reactive at one end and then these reactive copolymers are coupled to form the three-block copolymer ABA. These processes have the disadvantage, however, of producing homopolymers of A or B and/or copolymers AB, the latter particularly substantially affecting the mechanical properties of the three-block copolymer.

It is also well known to use bifunctional organolithium compounds in general as initiators in copolymerization processes for the preparation of these block copolymers. The initial preparation of these initiators, however, has required the presence of polar and/or complexing agents which have a deleterious effect during subsequent polymerization. Also, the functionality of the initiator is not always accurate, leading to the formation of undesired block copolymers AB and not the desired three-block copolymer ABA.

The present invention relates to a new and improved class of bifunctional organo-lithium compounds and to a method for their preparation in which no polar and/or complexing agents are used, which compounds when used as initiators in a copolymerization process avoid these problems of the prior art. These initiators are suitable for example for use in the preparation of polydienes having a stereoregularity equal to that of known polydienes. Also polymers including a polydiene block having reactive functions at both ends like hydroxyl, mercapto, carboxylic acid peroxide. More specific examples of these polymers and block copolymers are set forth below.

The new bifunctional organo-lithium compounds of the present invention are represented by the following formula:

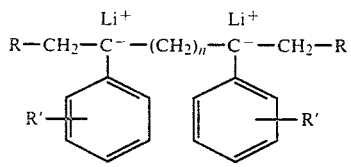

wherein R is an alkyl group having up to 5 carbon atoms, R' is either hydrogen or an alkyl group having up to 5 carbon atoms, and n is an integer of at least 2. Examples of R and R' are methyl, ethyl, propyl, butyl, tertbutyl, etc. Preferred values of n are integers of from 2 to 10 inclusive and more preferably, from 2 to 8. With values of n above 10, the synthesis of the compounds becomes more difficult, and the required starting materials are often more expensive and more difficult to obtain. Moreover, values of n above 8 do not generally provide any more advantageous results in subsequent polymerizations than compounds having a lower value.

In accordance with the present invention, these bifunctional organo-lithium compounds are prepared by first synthesizing an intermediate compound of the formula:

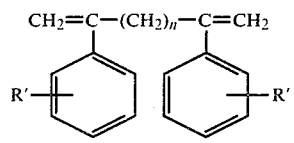

wherein n and R' are the same as defined above.

This intermediate compound can be prepared according to a known method that includes first reacting a diacid corresponding to the desired value for n; i.e., HOOC—(CH$_2$)$_n$—COOH with thionyl chloride to form the corresponding acid chloride. The acid halide is then condensed with benzene or nitrobenzene in the presence of aluminum trichloride (Friedel-Crafts reaction) to form the diketone:

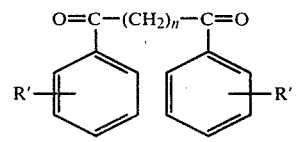

The diketone is then reacted with a brominated derivative of triphenylmethylphosphonium in the presence of diethylether and butyllithium or dimethylsulfoxide and sodium hydride to form the intermediate compound II.

These new intermediate compounds represented by formula II have common characteristics such as the optimal ultraviolet absorption ($\lambda_{max.}=237$ nm, $\epsilon_{max.}=2.15\times10^4$ mole $^{-1}$/1/cm$^{-1}$ and the NMR spectrum ($\delta$/TMS=5.0 and 5.3 ppm). The substances of formula II can moreover be characterized by their melting point (2,11-diphenyl 1,11-dodecadiene; 28° C.) and their boiling point (2,7-diphenyl 1,7-octadiene; 27° C. under 8 mm Hg).

The new organo-lithium compounds of the present invention as represented by formula I are then prepared by reacting in a non-polar solvent medium, such as a saturated or aromatic hydrocarbon, an alkyllithium compound (RLi) and the corresponding compound of formula II, the molar ratio of the alkyllithium compound to the compound of formula II being at least 2, so that the reaction equilibrium is shifted due to precipitation of the desired bifunctional organo-lithium compound.

For reasons of stability it is preferred to carry out the reaction at temperatures below 40° C. under normal pressure. The pressure can be below atmospheric pressure without any effect on the conduct of the reaction. For reasons of simplicity, the reaction is preferably carried out at room temperature under normal pressure.

In view of the sensitivity of the reactants used, it is essential to operate in the absence of deleterious gases present in the atmosphere such as oxygen, H₂O and CO₂. The reaction is therefore carried out in a vacuum or in an atmosphere of a gas which is inert to the reactants, for example argon or nitrogen.

The reaction is continued until all of the compound of formula II has reacted with the alkyllithium. The reaction is readily carried out continuously, the organolithium compound of formula I being then withdrawn continuously at the rate at which it is formed.

Whether the process is carried out discontinuously or continuously, the excess of the alkyllithium is removed from the reaction medium by filtration. The organolithium compound of formula I, which is obtained in the form of a precipitate, is then washed, preferably several times, and with the solvent of the reaction medium, to achieve a purity of about 98%. Above that value of the purity, the traces of impurities do not interfere with the subsequent uses of the compound, particularly if the compound is used as a polymerization initiator.

The new substances of the present invention as represented by formula I have common characteristics such as the optimal ultraviolet absorption ($\lambda_{max.}=335$ nm, $\epsilon_{max.}=1.5\times 10^4$ mole $^{-1}$/l/cm$^{-1}$).

As mentioned above new organo-lithium compounds of formula I are particularly useful as initiators in polymerization and copolymerization processes. One particular advantage in using the compound of this invention is that no polar and/or complexing agent has been used during the synthesis of the initiator. In the prior art, the bifunctional organo-lithium compounds were generally prepared in the presence of ethers or tertiary amines. Such agents, when used, remained in the polymerization initiator and effected subsequent polymerizations.

In the course of diene polymerization for example, the presence of a polar or complexing agent leads to 1,2-chains and, in the case of isoprene, to a polymer essentially consisting of 3,4-and 1,4-trans units which are not favorable to the production of good elastomers. As in the prior art, the organo-lithium initiators of this invention are insoluble in pure hydrocarbons. To avoid the inconvenience of polymerizing in a heterogeneous medium, the initiators are reacted with a small quantity of a diene (B), so that a polydiene (Li—B—Li) reactive at both ends is obtained.

When checking the polydispersity of that polymer by means of gel permeation chromatography, the chromatogram obtained comprises one sole peak and the macromolecular weights are weakly dispersed, impling that one sole species effected the propagation of the polymerization.

Examples of such dienes are butadiene, isoprene, 2,3-dimethyl-butadiene and 1,3-pentadiene. The reaction temperature is preferably below 100° C. and the reaction medium comprises a non-polar solvent of the precited type (saturated or aromatic hydrocarbon) and eventually an ethylenic comonomer.

Thus, there is provided a polydiene reactive at both ends, having a stereoregularity better than the known polydienes (the proportion of cis-1,4 units, as measured by nuclear magnetic resonance, is above 70 percent) and which can react in various ways. For example, ethylene oxide units can be added so as to convert the polydiene into a diol which can be used in the manufacture of polyurethanes.

By treating with CO₂, the polydiene can be converted into a dicarboxylic acid. By addition of oxygen, the polydiene is converted into a peroxide.

According to another particularly valuable application, the polydiene (Li—B—Li) reactive at both ends can be reacted with at least one anionically polymerizable ethylenic monomer to produce thermoplastic elastomers with improved mechanical properties. Suitable monomers for the purpose are for example styrene, methyl-methacrylate, α-methylstyrene and ethylene, of which styrene is preferred. There are obtained in this way three-block copolymers of the ABA type, wherein the A blocks are derived from the polymerizable ethylenic monomer (s) used and the middle B block is a polydiene such as polyisoprene or polybutadiene. The thermomechanical properties of these block copolymers, which are thermoplastic elastomers, are superior to those of previously known products of this kind. They are in fact pure copolymers.

To illustrate the invention more specifically, reference is made to the following examples. These examples illustrate the preparation of the intermediate compounds represented by formula II as well as the novel bifunctional organo-lithium compounds of the present invention represented by the formula I and their use as polymerization initiators in the production of polymers and block copolymers.

The examples are merely illustrative and are to be understood as not limiting the scope and underlying principles of the invention in any way.

EXAMPLE I

PREPARATION OF INTERMEDIATE COMPOUND OF FORMULA II 324 grams of a diacid, sebacic acid, were introduced into a three-necked flask equipped with a dropping funnel, a stirrer and a condenser. 381 grams of thionyl chloride were then added slowly. The mixture was heated for 6 hours at a reflux temperature of about 78° C. Excess thionyl chloride was then distilled off. Sebacyl dichloride, having a b.p. of 165° C. under 11 mm Hg was obtained.

145.5 grams of finely divided AlCl₃, and 241 cc of anydrous benzene were poured into a three-necked flask equipped with a dropping funnel, a stirrer and a condenser. After the aluminum chloride had dissolved completely, 116 grams of the prepared sebacyl dichloride were added slowly while maintaining the temperature at about 45° C. At the end of the addition, the temperature was kept at 50° C., and stirring was continued for 6 hours.

After cooling the solution, hydrolysis was effected by the addition of a mixture of water and ice (20 cc of conc. hydrochloric acid). A white-precipitate appeared, insoluble in both phases.

The precipitate was filtered off and washed with diethyl ether. The diketone, 1,10-diphenyl-1,10 decadione (a crystalline white product) was obtained with a yield of 80%.

Triphenylmethylphosphonium bromide was first prepared by pouring 200 ml of anhydrous benzene into a flask equipped with a dropping funnel and a stirrer. 157.7 grams of diphenylphosphine were then dissolved in the benzene. 45.5 cm³ of methyl bromide were added at −15° C. The mixture was allowed to return to room temperature and was stirred for 72 hours. A white precipitate was collected and washed with 500 ml of hot benzene. It was dried in a vacuum oven at 100° C. for 24 hours. Triphenylmethylphosphonium bromide, m.p. 232.5° C. was obtained with a yield of 99%.

A stream of anhydrous nitrogen was passed through the whole apparatus, comprising a one litre three-necked flask equipped with a condenser, a dropping funnel, a stirrer and a gas inlet, throughout the entire operation. 72 grams of the triphenylmethylphosphonium bromide were added to an ether solution of n-butyllithium (0.2 mole). The solution was stirred for 4 hours at room temperature and an orange-yellow solution was obtained. 32.2 g of 1, 10-diphenyl-1, 10-decadione, prepared above, were then added. The solution lost its color. The solution was then heated under reflux for 24 hours and the precipitate (unreacted diketone and phosphine oxide) was filtered off as soon as the solution had reached room temperature.

The precipitate was washed with diethyl ether, then with petroleum ether. The solution was passed twice through an activated alumina column.

The physical characteristics of the 2,11-diphenyl 1,11-dodecadiene thus obtained are as follows:

Melting point
M.p. = 76° C.
Ultraviolet spectrum (in hexane)
$\lambda$max 237 nm
$\epsilon$max $2.15 \times 10^4$ mole$^{-1}$/l/cm$^{-1}$ (Beer's law has been verified between $10^{-2}$ and $10^{-6}$ mole/l.

These results showed that two $\alpha$-methyl-styrene units per molecule were present.

NMR spectrum: $^1$H 60 Hz
(in deuterated acetone, internal reference tetramethylsilane TMS)

In addition to the humps corresponding to the methylene and aromatic protons, two signals, characteristic of the vinylidene groups, were observed: $\delta$/TMS = 5.6 and 5.9 ppm.

EXAMPLE 2

PREPARATION OF ORGANO-LITHIUM COMPOUND OF FORMULA I

All the operations were carried out in the absence of air. Tertbutyllithium was purified by sublimation in a vacuum and then dissolved in hexane.

The 2,11-diphenyl 1,11-dodecadiene of Example 1 was dissolved in hexane and the solution was contacted with sodium. The prepared solutions were mixed in such a way that there is an excess of tertbutyllithium and the initiator 2,11- dilithio-2,11-diphenyl-1,12-ditertbutyl dodecane precipitated after three days at room temperature. The supernatant solution had an organge-red color which exhibited an absorption maximum at 315 nm. The insoluble initiator was collected in the form of a brownish-red compound.

EXAMPLE 3

The compound prepared in Example 2 was first checked to confirm that it was about 98% pure and thus essentially free of mono-functional species. For this purpose, it was washed additionally with hexane and the efficiency of the washing checked by examining the increase in the optical density at 315 nm.

Isoprene was then brought into contact with the purified initiator. The initially brownish-red precipitate changed to yellow and then dissolved in the as yet unconverted isoprene to give a yellow solution. A solution in hexane of an organo-lithium compound reactive at both ends, was thus obtained.

EXAMPLE 4

In this example, the initiator prepared in Example 2 was used for the stereospecific polymerization of isoprene, the reaction medium being hexane.

In this way, the functionality of the isopropenyllithium was also confirmed. It is known that in anionic polymerization, the average molecular weight is, in the case of a bifunctional initiator, related to the amount of initiator and of monomer by the equation:

$$\overline{M}_n = (2m/c)$$

where m is the amount of monomer and c the amount of initiator.

In practice, m is determined by a weight measurement and c by a spectrophotometric measurement.

In experiments A, B and C of the Table below, the polymerization of isoprene was carried out and in experiment D, a styrene/isoprene/styrene three-block copolymer was prepared.

Various values of m and c have been used in these experiments and excellent agreement is found between the theoretical values and the experimental values of $\overline{M}_n$ (determined by osmometry).

The various results given above demonstrate that the bifunctional initiator of Example 2 is effective as an anionic polymerization initiator in a polymerization medium which consists only of a hydrocarbon.

Experiments relating to the microstructure of the polyisoprenes obtained were also carried out. Thus, the various types of units present in the macromolecules were determined by analyzing the carbon 13 and $^1$H proton (100 MHz) NMR spectra.

These determinations concerning experiments B and C are indicated in the table below.

| EXPERIMENT | $\overline{M}_n$ | 1,4-Cis % | 1,4-Trans % | 3,4 % |
|---|---|---|---|---|
| A | 7,000 | | | |
| B | 132,000 | 73.0 | 21.3 | 5.7 |
| C | 71,000 | 71.9 | 22.7 | 5.4 |
| D | 89,000 | | | |

This invention in its broader aspects is not limited to the specific details shown and described and departures may be made from such details without departing from the principles of the invention and without sacrificing its chief advantages.

We claim:

1. An intermediate compound for polymerization initiators, said compound having the formula:

$$CH_2=C-(CH_2)_n-C=CH_2$$

(with R' substituents on the two phenyl rings attached to the C atoms)

wherein n is between 2 and 10 and R' is hydrogen or an alkyl group having 1 to 5 carbon atoms.

2. The intermediate compound of claim 1, wherein said compound is 2,11-diphenyl 1,11 docecadiene.

3. The intermediate compound of claim 1, wherein said compound is 2,7-diphenyl 1,7, octadiene.

* * * * *

UNITED STATES PATENT AND TRADEMARK OFFICE
CERTIFICATE OF CORRECTION

PATENT NO. : 4,181,684

DATED : January 1, 1980

INVENTOR(S) : PIERRE SIGWALT ET AL

It is certified that error appears in the above-identified patent and that said Letters Patent are hereby corrected as shown below:

Column 1, line 47, change "Also" to --also--; change the period (.) to semi-colon (;);

Column 3, line 59, delete "better than" and substitute --equal to--therefor;

Column 5, line 21, delete "76" and substitute --28-- therefor;

Column 5, lines 34 and 35, delete "5.6 and 5.9" and substitute --5.0 and 5.3-- therefor.

Signed and Sealed this

Ninth Day of December 1980

[SEAL]

Attest:

SIDNEY A. DIAMOND

Attesting Officer

Commissioner of Patents and Trademarks